United States Patent
Podany

(10) Patent No.: US 10,085,796 B2
(45) Date of Patent: Oct. 2, 2018

(54) BIPOLAR ELECTROSURGICAL CUTTER WITH POSITION INSENSITIVE RETURN ELECTRODE CONTACT

(71) Applicant: Medtronic Advanced Energy LLC, Minneapolis, MN (US)

(72) Inventor: Vaclav O. Podany, New Fairfield, CT (US)

(73) Assignee: Medtronic Advanced Energy LLC, Minneapolis, MN (US)

(*) Notice: Subject to any disclaimer, the term of this patent is extended or adjusted under 35 U.S.C. 154(b) by 48 days.

(21) Appl. No.: 15/415,430

(22) Filed: Jan. 25, 2017

(65) Prior Publication Data

US 2017/0224408 A1    Aug. 10, 2017

Related U.S. Application Data

(62) Division of application No. 13/046,670, filed on Mar. 11, 2011, now Pat. No. 9,592,090.

(Continued)

(51) Int. Cl.
*A61B 18/14* (2006.01)
*A61B 18/12* (2006.01)
(Continued)

(52) U.S. Cl.
CPC ........ *A61B 18/148* (2013.01); *A61B 18/1233* (2013.01); *A61B 2017/00199* (2013.01);
(Continued)

(58) Field of Classification Search
CPC . A61B 18/12; A61B 18/1233; A61B 18/1266; A61B 18/14; A61B 18/1442; A61B 18/1445; A61B 18/1448; A61B 18/148; A61B 2018/00011; A61B 2018/00083; A61B 2018/00589; A61B 2018/00601; A61B 2018/1472;
(Continued)

(56) References Cited

U.S. PATENT DOCUMENTS 2,888,928 A    6/1959    Seiger
3,682,130 A    8/1972    Jeffers
(Continued)

FOREIGN PATENT DOCUMENTS

WO    WO96/04955 A2    2/1996
WO    WO2007-037785    4/2007
WO    WO2010/141417    12/2010

*Primary Examiner* — Michael Peffley
*Assistant Examiner* — Khadijeh Vahdat
(74) *Attorney, Agent, or Firm* — Christopher & Weisberg, P.A.

(57) ABSTRACT

A bipolar electrosurgical device includes a handle and an elongated end effector coupled to the handle. The end effector includes an elongated, insulating body having first and second electrodes disposed thereon. The first and second electrodes are separated at the distal end of the insulating body, and a cavity formed in the distal end of the effector is positioned between the first and second electrodes. A fluid-delivery tube is positioned on the body to deliver a conductive fluid to the distal end, adjacent the cavity. During use of the electrosurgical device, delivery of the conductive fluid facilitates formation of an electrical coupling between the electrodes via the tissue being treated.

12 Claims, 12 Drawing Sheets

Related U.S. Application Data

(60) Provisional application No. 61/313,056, filed on Mar. 11, 2010.

(51) Int. Cl.
  *A61B 18/00* (2006.01)
  *A61B 18/16* (2006.01)
  *A61B 17/00* (2006.01)

(52) U.S. Cl.
  CPC ............... *A61B 2017/00973* (2013.01); *A61B 2018/00011* (2013.01); *A61B 2018/00083* (2013.01); *A61B 2018/00589* (2013.01); *A61B 2018/00601* (2013.01); *A61B 2018/1472* (2013.01); *A61B 2018/167* (2013.01)

(58) Field of Classification Search
  CPC .... A61B 2018/167; A61B 2017/00199; A61B 2017/00973
  USPC ..................................................... 606/21–50
  See application file for complete search history.

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,009,656 A * | 4/1991 | Reimels ............. A61B 18/1482 606/48 |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Milder |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,196 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |

(56) References Cited

U.S. PATENT DOCUMENTS

| | | |
|---|---|---|
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,637,090 A | 9/1997 | McGee et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,928,191 A | 9/1999 | Houser et al. |
| 5,954,661 A | 9/1999 | Greenspon et al. |
| 5,971,980 A | 10/1999 | Sherman |
| 5,971,983 A | 10/1999 | Lesh |
| 5,975,919 A | 11/1999 | Arnett et al. |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,528 B1 | 4/2001 | Koblish et al. |

(56) References Cited

U.S. PATENT DOCUMENTS

| | | |
|---|---|---|
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| RE5,697,536 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | Bloom et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,691,050 B2 | 4/2010 | Gellman |
| 7,727,232 B1 | 6/2010 | Maurer et al. |
| 7,736,361 B2 | 6/2010 | Palanker |
| 7,811,282 B2 | 10/2010 | McClurken |
| 7,815,634 B2 | 10/2010 | Bloom et al. |

(56) References Cited

U.S. PATENT DOCUMENTS

| | | |
|---|---|---|
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Bloom et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,323,276 B2 | 12/2012 | Palanker et al. |
| 8,348,946 B2 | 1/2013 | McClurken |
| 8,361,068 B2 | 1/2013 | McClurken |
| 8,388,642 B2 | 3/2013 | Muni et al. |
| 8,414,572 B2 | 4/2013 | Davison et al. |
| 8,475,455 B2 | 7/2013 | McClurken |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2005/0273097 A1 | 12/2005 | Ryan |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0111709 A1 | 5/2006 | Goble et al. |
| 2007/0049920 A1 | 3/2007 | Bloom et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0058821 A1 | 3/2008 | Maurer et al. |
| 2008/0071270 A1 | 3/2008 | Desinger et al. |
| 2008/0103494 A1* | 5/2008 | Rioux ............... A61B 18/1482 606/37 |
| 2008/0207208 A1 | 8/2008 | Schutz |
| 2008/0262489 A1 | 10/2008 | Steinke |
| 2009/0222001 A1 | 9/2009 | Greeley et al. |
| 2009/0264879 A1 | 10/2009 | Bloom et al. |
| 2009/0306655 A1 | 12/2009 | Stangeness |
| 2010/0069904 A1 | 3/2010 | Cunningham |
| 2010/0100095 A1 | 4/2010 | Bloom et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |

\* cited by examiner

BIPOLAR ELECTROSURGICAL CUTTER WITH POSITION INSENSITIVE RETURN ELECTRODE CONTACT

CROSS-REFERENCE TO RELATED APPLICATION

This application is a divisional of patent application Ser. No. 13/046,670, filed Mar. 11, 2011, now U.S Pat. No. 9,592,090, entitled BIPOLAR ELECTROSURGICAL CUTTER WITH POSITION INSENSITIVE RETURN ELECTRODE CONTACT, and is related to and claims priority to Provisional Application No. 61/313,056, filed Mar. 11, 2010, the entirety of which is incorporated herein by reference.

STATEMENT REGARDING FEDERALLY SPONSORED RESEARCH OR DEVELOPMENT n/a

TECHNICAL FIELD

This invention relates generally to the field of medical systems, devices and methods for use upon a human body during surgery. More particularly, the invention relates to surgical systems, devices and methods that provide plasma-mediated cutting, fragmentation and evaporation/vaporization of tissue during surgery such as plastic, microsurgery, reconstructive, neurological and any other surgery where it is desirable to use a bipolar configuration without the need for undue manipulation of the angle of application to establish electrical contact

BACKGROUND

When electrosurgical cutting with an electrode is initiated, the tissue presents a low impedance path to the Radio Frequency (RF) current so that, at a given voltage, a significant amount of RF current (and RF power) may flow through the tissue. When this current heats the tissue from body temperature to greater than about 100° C., the fluid in the tissue starts vaporizing. The impedance begins increasing as the electrode is enveloped by a thin vapor bubble/layer.

Once the vapor envelops the electrode, it interrupts the current and the full voltage of the generator may be applied across the thin vapor layer to create a high electric field in the vapor bubble. This high electric field exerts force on the ions present in the vapor, accelerating them and establishing the current flow across the vapor gap. Impedance is understood to start decreasing (ionization phase) as a plasma develops. As the ions are accelerated, they are understood to collide with the molecules present in the vapor bubble, further ionizing them and leading to spark discharge. As the voltage across the vapor gap is present, it is understood to further accelerate the ions in the plasma, increasing their kinetic energy and thus temperature of the plasma which may eventually lead to avalanche ionization, high energy and arc discharge.

Many RF systems use a monopolar configuration for electrosurgical cutting. Such a device has an active electrode at its tip that is applied to the tissue to be cut. The return electrode is often in the form of a ground pad dispersive electrode that is placed on a patient's body in a different location than the area of surgery. An electrical circuit forms between the active electrode and return electrode through the patient. Since the path of the current through the patient is not precisely defined and is dependent on the local conditions of the tissue, the monopolar configuration is not the best to use in the proximity of sensitive organs or structures.

An electrosurgical device in a bipolar configuration, with the return electrode next to the active electrode, is a much safer device in such circumstances. An electrical circuit forms between the two electrodes, removing the need for current to flow through a patient's body to the ground pad as the monopolar configuration requires. One shortcoming of the bipolar configuration, however, is its need to establish two points of contact with the tissue to initiate cutting. The two-point contact is dependent on the angle of the handpiece with respect to the tissue surface. This dependence on angle may make it necessary to tilt the handpiece to establish a good contact and ignite the plasma.

One bipolar electrosurgical device addressed this problem with a spring-loaded return electrode to provide a self-compensating function. Coagulated blood or accumulated tissue may impede the proper function of such a device, however. Another variation involves coblation, which uses saline as a return electrode. This approach, however, requires the electrode to be submerged in saline for the duration of the task.

SUMMARY

The invention is a bipolar electrosurgical device that includes a handle and an elongated end effector coupled to the handle. The end effector (e.g., an elongated member for carrying bipolar electrodes to a surgical site for contacting tissue and performing electrosurgery) includes an elongated, insulating body having a proximal end coupled to the handle such that the body extends away from the handle toward a distal end. A first electrode (e.g., a cutting electrode) and a second electrode (e.g., a return electrode) are disposed along the insulating body. The first and second electrodes are separated at the distal end of the insulating body, and a cavity formed in the distal end of the effector is positioned between the first and second electrodes. A fluid-delivery tube is positioned on the body to deliver a conductive fluid to the distal end the insulating body adjacent the cavity.

An electrosurgical power generator (also called a voltage source, power supply or waveform generator) may be coupled to the proximal end of the device to provide a voltage to the electrodes of the end effector. During use of the electrosurgical device, delivery of the fluid facilitates formation of an electrical coupling between the first electrode and the second electrode via the tissue being treated, adjacent the distal end of the insulating body for performance of an electrosurgical procedure.

In a first embodiment, the end effector is wedge-shaped with the cutting electrode at the narrow base of the wedge-shaped effector extending at least a portion of the way along the base, and a return electrode disposed at least partially in the cavity formed in the distal end of the effector. A tube or passage through the body of the end effector delivers fluid to the cavity. The insulating body of the effector separates the cutting and return electrodes.

The cutting electrode may be formed from a sheet of metal that is folded or bent around the apex edge of the wedge-shaped effector. Further, the edge formed from the folding of the metal sheet may be sharpened to form a sharp edge that has a thickness of about 0.005 inches to 0.10 inches (0.12 millimeters to 0.25 millimeters). Alternatively, the cutting electrode may be formed, for example, from a rounded, cylindrical-shaped conductor or wire with a radius less than about 20 mils and preferably about five (5) mils.

In another embodiment, the end effector has an insulating body portion with a cross-sectional shape that is a substantially flat rectangle or blade. The first electrode is disposed on a minor edge (i.e., the narrow side or edge of the rectangle) of the blade-shaped body portion, and the second electrode is disposed on the opposite minor edge. Both electrodes extend along the length of the body portion to the distal end. At the distal end, separation is maintained between the two electrodes. A cavity or dimple is formed in the distal end of the body portion between the electrodes. In one example embodiment, the electrodes are formed by metallized layers on the insulating body.

In this blade-shaped embodiment of the end effector, the first electrode may comprise a wire having, for example, a diameter less than about one mm. The wire may be attached to the metallized layer or may be used in lieu of the metallized layer. Also, in this example embodiment, a fluid-delivery tube may be attached to the body portion of the end effector at the second electrode (i. e., the return electrode). The fluid-delivery tube may be made from a conductive material such as metal or a conductive polymer. In one embodiment, the fluid-delivery tube may act as the return electrode.

Another aspect of the invention includes a method of cutting biological tissue. The method involves initiating flow of an electrically conductive fluid to a distal end of the bipolar electrosurgical device. Electrical energy is applied between the first electrode and the second electrode on the bipolar electrosurgical device. The bipolar electrosurgical device is then applied to the biological tissue such that the first electrode near the distal end of the bipolar electrosurgical device is in direct contact with the biological tissue. This will result in formation of an electrical arc adjacent the distal end of the bipolar electrosurgical device. Thereafter, the flow of the electrically conductive fluid may be terminated without affecting the arc. The arc is maintained to cut the biological tissue.

It is an advantage that the electrosurgical device of the invention is able to establish a conductive path between the electrodes via the tissue with less sensitivity to handpiece angle (i.e., the angle at which the hand-held electrosurgical device is held with respect to the tissue being treated) as compared with prior devices.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
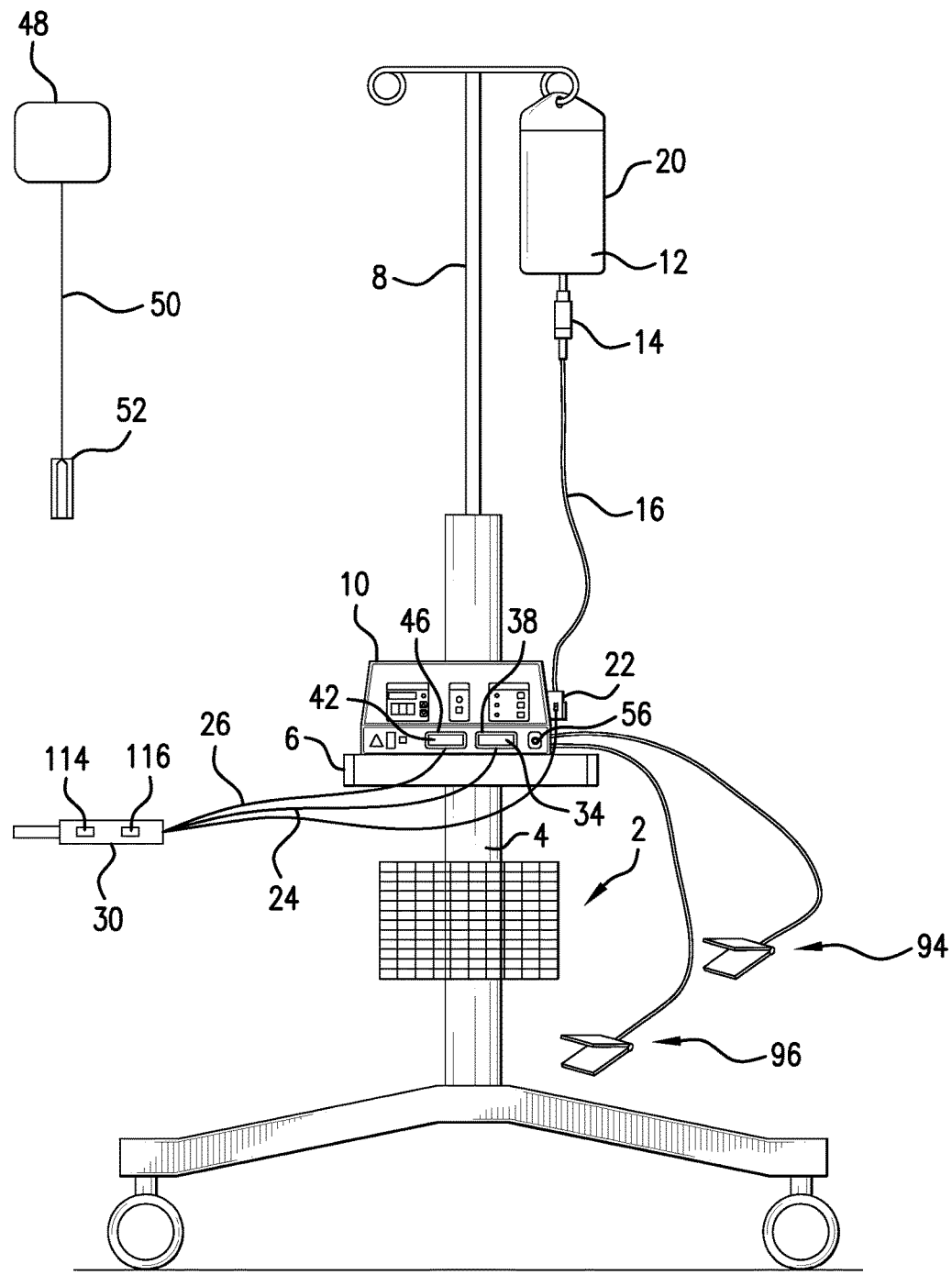
FIG. 1 is a front view of one embodiment of a system of the present invention having an exemplary electrosurgical unit in combination with a fluid source and handheld electrosurgical device.

The features and advantages of the present invention will become apparent from the detailed description set forth below, when taken in conjunction with the drawings in which like reference numbers indicate identical or functionally similar elements. Throughout the description, like reference numerals and letters indicate corresponding structure throughout the several views. Features between the various exemplary embodiments described in this specification are interchangeable and are not exclusive to the embodiment in which they are described. Any use of the terms "distal" and "proximal" are made in reference from the user of the device, and not the patient.

The invention provides systems, devices and methods for cutting, coagulating and providing hemostasis. The invention will now be discussed with reference to the figures.

FIG. 1 shows a front view of an exemplary embodiment of a system of the present invention having an electrosurgical unit 10 in combination with a handheld electrosurgical device 30, and a fluid source 20 and fluid delivery arrangement. A movable cart 2 has a support member 4 comprising a hollow cylindrical post which carries a platform 6, comprising a pedestal table to provide a flat, stable surface for location of the electrosurgical unit 10. As shown, cart 2 may further comprise a fluid source carrying pole 8 having a cross support provided with loops at its ends to provide a hook for carrying fluid source 20.

Fluid source 20 comprises a bag of fluid. Fluid 12 flows from fluid source 20 through a drip chamber 14 after a spike located at the end of drip chamber 14 penetrates the bag. Fluid 12 may then flow through flexible delivery tubing 16 to handheld electrosurgical device 30. The fluid delivery tubing 16 is made preferably from a polymer material. As shown in FIG. 1, the fluid delivery tubing 16 may pass through pump 22. Pump 22 may comprise a peristaltic pump and, more specifically, a rotary peristaltic pump.

With a rotary peristaltic pump, a portion of the delivery tubing 16 may be loaded into the pump head by raising and lowering the pump head in a known manner. Fluid 12 may then be conveyed within the delivery tubing 16 by waves of contraction placed externally on the tubing 16. The waves of contraction are produced mechanically, typically by rotating pinch rollers which rotate on a drive shaft and intermittently compress the tubing 16 against an anvil support. Peristaltic pumps are generally preferred, because the electro-mechanical force mechanism, here rollers driven by electric motor, does not make contact with the fluid 12, thus reducing the likelihood of inadvertent contamination.

In other embodiments, pump 22 may be separate instead of integrated with electrosurgical unit 10. In still other embodiments, pump 22 may be eliminated and the fluid flow rate may be manually controlled. Such manual control may be by the user of device 10 or another member of the surgical team with a roller (pinch) clamp or other clamp provided with device 10. The clamp is configured to act upon and compress the tubing 16 and control flow in a manner known in the art.

The fluid may particularly comprise an electrically conductive fluid such as saline solution, and even more specifically, normal (physiologic) saline. Although the description herein may make reference to saline as the fluid 12, other electrically conductive fluids can be used in accordance with the invention. For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringer's solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, the conductive fluid is a solution that conducts electricity via, for example, an electrolyte (i.e., a substance such as a salt, acid or base that dissociates into electrically charged ions when dissolved in a solvent, such as water, resulting in a solution comprising an ionic conductor).

The use of conductive fluids may provide certain advantages over the use of a dry electrode including, for example, reduced occurrence of tissue sticking to the electrode of device 30, reduced smoke generation, and increased cooling of the electrode and/or tissue. A conductive fluid may also be particularly suited to provide better coagulation and hemostasis of tissue, given the desire to more widely disperse the electrical energy over a wider area of tissue.

Electrosurgical unit 10 may be configured to provide both monopolar and bipolar power output, and may include a lock out feature which prevents both monopolar and bipolar output from being activated simultaneously.

During monopolar operation, a first electrode, often referred to as the active electrode, may be disposed on the handheld portion of the electrosurgical device, while a second electrode, often referred to as the indifferent or neutral electrode, may be provided in the form of a ground pad dispersive electrode located on the patient (also known as a patient return electrode), typically on the back or other suitable anatomical location. An electrical circuit may be formed between the active electrode and ground pad dispersive electrode with electrical current flowing from the active electrode through the patient to the ground pad dispersive electrode in a manner known in the art.

During bipolar operation, the ground pad electrode located on the patient is not required, and a second electrode providing an electrical pole may be disposed on the handheld portion of the device. An alternating current electrical circuit may then be created between the first and second electrical poles of the device. Consequently, alternating current will typically not flow through the patient's body to a ground pad electrode as in monopolar operation, but rather through a localized portion of tissue between the poles of the bipolar device.

As shown in FIG. 1, depending on whether electrosurgical device 30 is a bipolar or monopolar device, device 30 may be connected to electrosurgical unit 10 via electrical cable 24 or cable 26. Cable 24 has a plug 34 which connects to bipolar mode output receptacle 38 of electrosurgical unit 10. Cable 26 has a plug 42 which connects to the monopolar mode output receptacle 46 of electrosurgical unit 10. When electrosurgical unit 10 is used in monopolar mode, an additional cable 50 is utilized to connect a ground pad dispersive electrode 48 to the ground pad receptacle 56 of the electrosurgical unit 10 via a connector 52 of cable 50.

Figure 2:
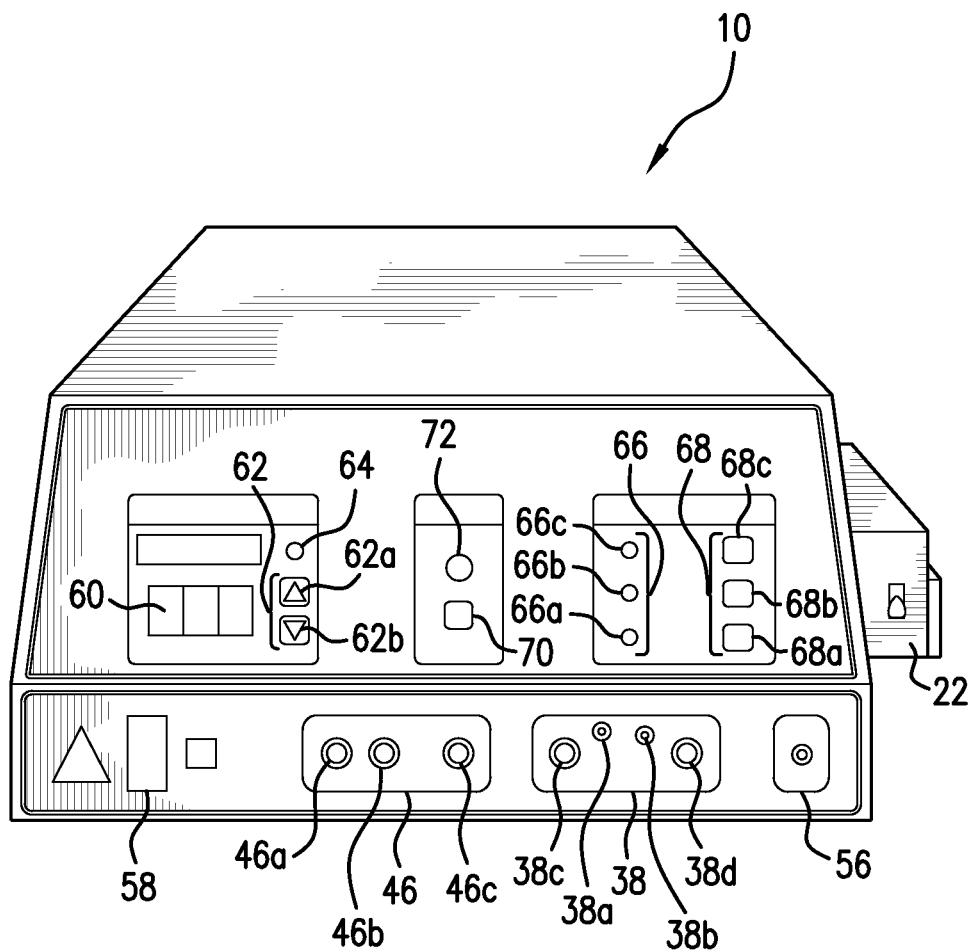
FIG. 2 a front perspective view of the electrosurgical unit of FIG. 1.

FIG. 2 shows the front panel of the exemplary electrosurgical unit 10. A power switch 58 may be used to turn the electrosurgical unit 10 on and off. After turning the electrosurgical unit 10 on, an RF power setting display 60 may be used to display the RF power setting numerically in watts. The power setting display 60 may further comprise a liquid crystal display (LCD).

Electrosurgical unit 10 may further comprise an RF power selector 62 comprising RF power setting switches 62a, 62b which may be used to select the RF power setting. Pushing the switch 62a will increase the RF power setting, while pushing the switch 62b will decrease the RF power setting. Additionally, electrosurgical unit 10 may include an RF power activation display 64 comprising an indicator light which will illuminate when RF power is activated, either via a hand switch on device 30 (e.g. shown in FIG. 1 as monopolar or bipolar cut switch 114 or coagulate switch 116, depending on whether the device is a monopolar or bipolar device, respectively) or a footswitch (e.g. shown in FIG. 1 as monopolar or bipolar cut footswitch 94 or coagulate footswitch 96, depending on whether the device is a monopolar or bipolar device, respectively). Switches 62a, 62b may comprise membrane switches. It should be understood that, while only one RF power selector 62 is shown, electrosurgical unit 10 may have two such RF power selectors with one each for monopolar and bipolar power selection.

In addition to having RF power setting display 60, electrosurgical unit 10 may further include a fluid flow rate setting display 66. Flow rate setting display 66 may comprise three indicator lights 66a, 66b and 66c with first light 66a corresponding to a fluid flow rate setting of low, second light 66b corresponding to a fluid flow rate setting of medium (intermediate), and third light 66c corresponding to a flow rate setting of high. One of these three indicator lights will illuminate when a fluid flow rate setting is selected.

Electrosurgical unit 10 may further include a fluid flow selector 68 comprising flow rate setting switches 68a, 68b and 68c used to select or switch the flow rate setting. Three push switches may be provided with first switch 68a corresponding to the fluid flow rate setting of low, second switch 68b corresponding to a fluid flow rate setting of medium (intermediate) and third switch 68c corresponding to a flow rate setting of high. Pushing one of these three switches will select the corresponding flow rate setting of either low, medium (intermediate) or high. The medium, or intermediate, flow rate setting may be automatically selected as the default setting if no setting is manually selected. Switches 68*a*, 68*b* and 68*c* may comprise membrane switches.

Before starting a surgical procedure, it may be desirable to prime device 30 with fluid 12. A priming switch 70 may be used to initiate priming of device 30 with fluid 12. Pushing switch 70 once may initiate operation of pump 22 for a predetermined time period to prime device 30. After the time period is complete, the pump 22 may shut off automatically. When priming of device 30 is initiated, a priming display 72 comprising an indicator light may illuminate during the priming cycle.

In an example embodiment, electrosurgical unit 10 is an electrosurgical power generator (also called a voltage source, power supply or waveform generator) which produces a pulsed radio frequency (RF) waveform. The waveform can include a burst of biphasic pulses followed by a burst interval during which no pulses are present. Each pulse may have an opposite electrical polarity to that of a previous pulse (i.e., the pulses are charge balanced biphasic). Example characteristics of the power generator include a peak power output in a range of about 0.5 kW (kilowatts) to 2.5 kW, a peak voltage output in a range of about 200 volts to 1,000 volts, a burst frequency in a range of about 0.5 kHz to 12 kHz (kilohertz), and a burst duty cycle in a range of about 5% to 95%. In another example embodiment, electrosurgical unit 10 is an electrosurgical power generator as described in U.S. Pat. No. 7,357,802, which is incorporated herein by reference. Electrosurgical device 30 of the present invention is described in further detail below with reference to FIGS. 3-8. It should be understood that while electrosurgical device 30 and electrosurgical unit 10 are described herein as being used together, a person skilled in the relevant art will understand that electrosurgical device 30 may be used with other electrosurgical units, and electrosurgical unit 10 may be used with other electrosurgical devices.

Figure 3:
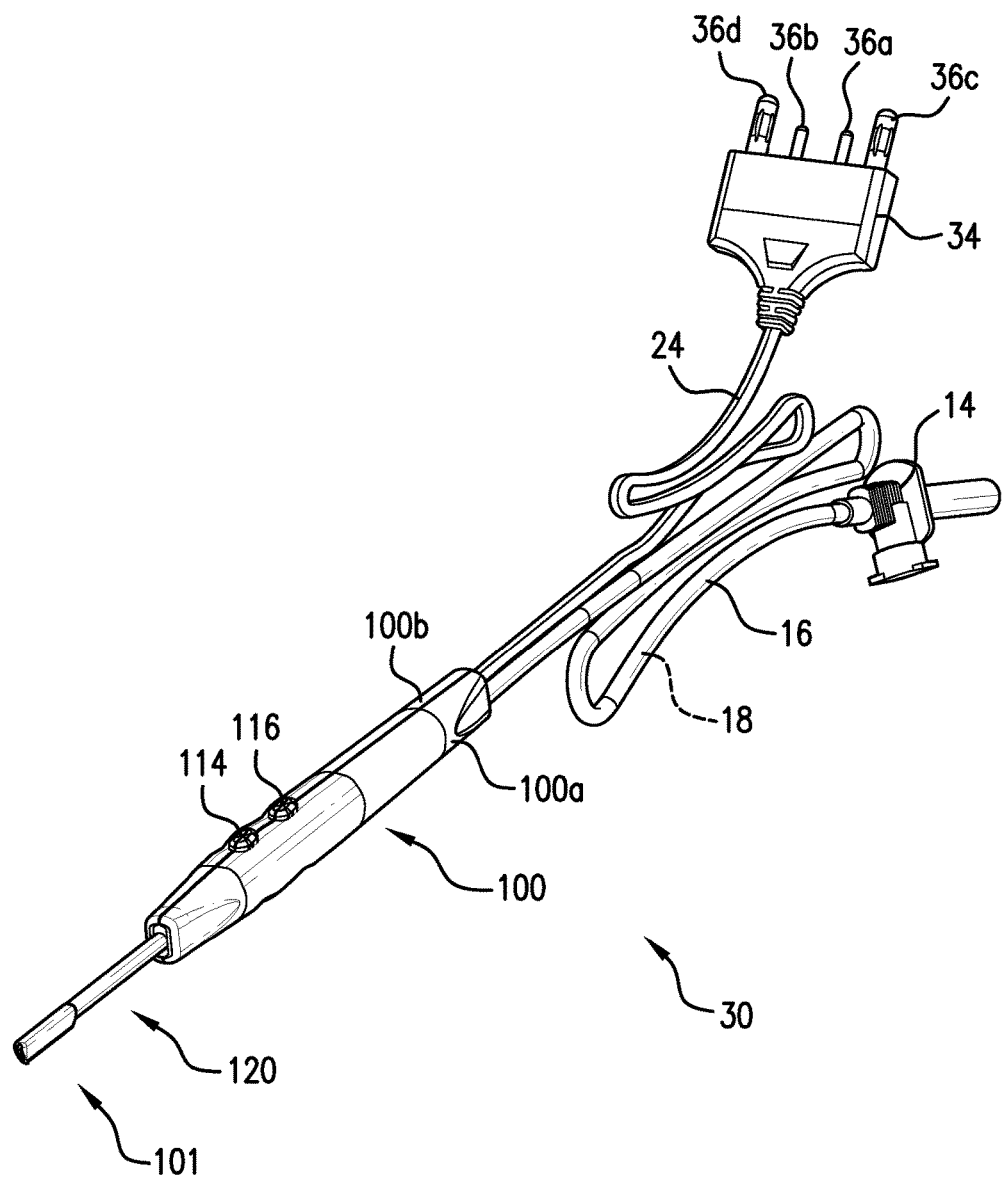
FIG. 3 is a perspective view of an electrosurgical device according to the present invention.

As shown in FIG. 3, exemplary device 30 is a bipolar device which comprises an elongated handle 100 comprising mating handle portions 100*a* and 100*b*. Handle 100 is slender, along with the rest of device 30, to enable a user of device 30 to hold and manipulate device 30 between the thumb and index finger like a pen-type device. Handle 100 may comprise a sterilizable, rigid, non-conductive material, such as a polymer (e.g., polycarbonate).

During use of device 30, fluid 12 from fluid source 20 may flow through a tubular fluid passage which may be provided by various structures. In the present embodiment, fluid 12 from the fluid source 20 may first flow through lumen 18 of delivery tubing 16. Fluid 12 may also flow through a lumen of a special pump tubing segment designed to operate specifically with pump 22, which may be spliced in between portions of delivery tubing 16 and connected thereto at each end.

Device 30 includes cable 24 which is connectable to electrosurgical unit 10 to provide device 30 with bipolar power output from electrosurgical unit 10. Cable 24 of device 30 comprises four insulated wire conductors connectable to bipolar power output receptacles 38*a*, 38*b*, 38*c*, 38*d* (see FIG. 2) of electrosurgical unit 10 via four banana (male) plug connectors 36*a*, 36*b*, 36*c*, 36*b*. The banana plug connectors 36*a*, 36*b*, 36*c*, 36*d* are each assembled with the insulated wire conductors within the housing of plug 34 in a known manner. Plug connectors 36*a*, 36*b* are electrically coupled by wire conductors to hand switches 114, 116, respectively, in a known manner. Plug connector 36*c* is electrically coupled by a wire conductor to tubular shaft member 120, which is electrically coupled to electrode 134. Plug connector 36*d* is electrically coupled by a wire conductor to electrode 136. Electrodes 134 and 136 provide a bipolar pair of electrodes. Electrode 136 may be referred to as an active electrode, and electrode 134 may be referred to as a return electrode, due to the differences in surface area.

Figure 4:
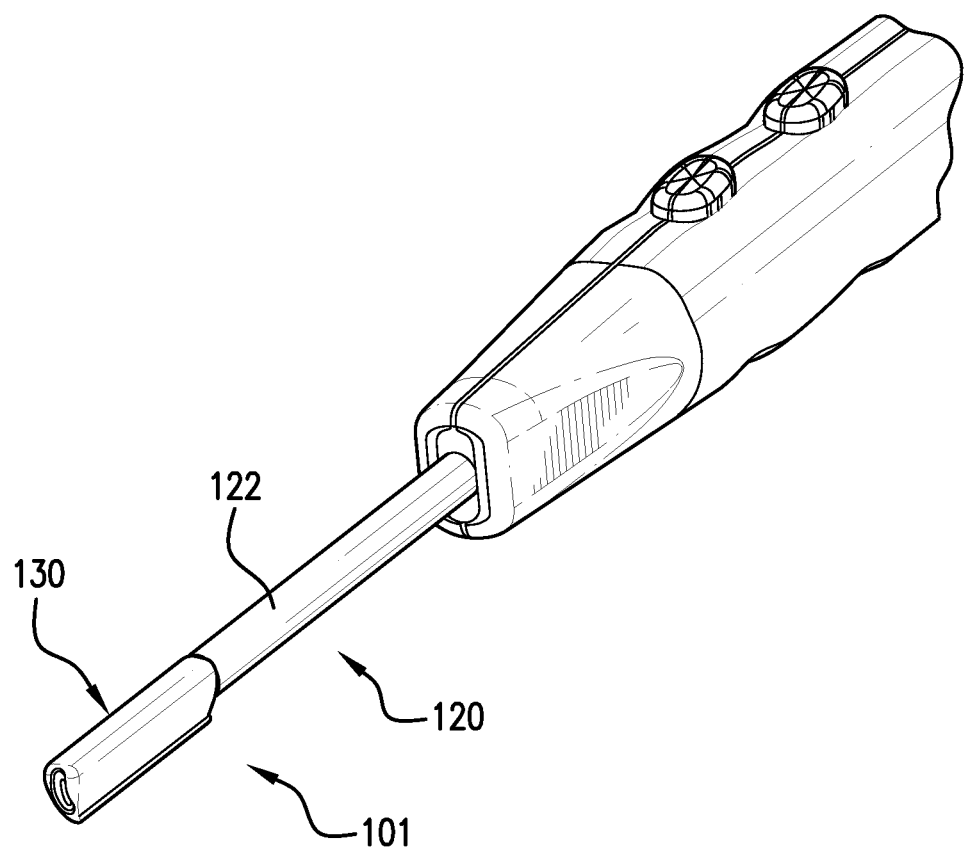
FIG. 4 is a perspective view of a distal end portion of the electrosurgical device of FIG. 3.
Figure 5:
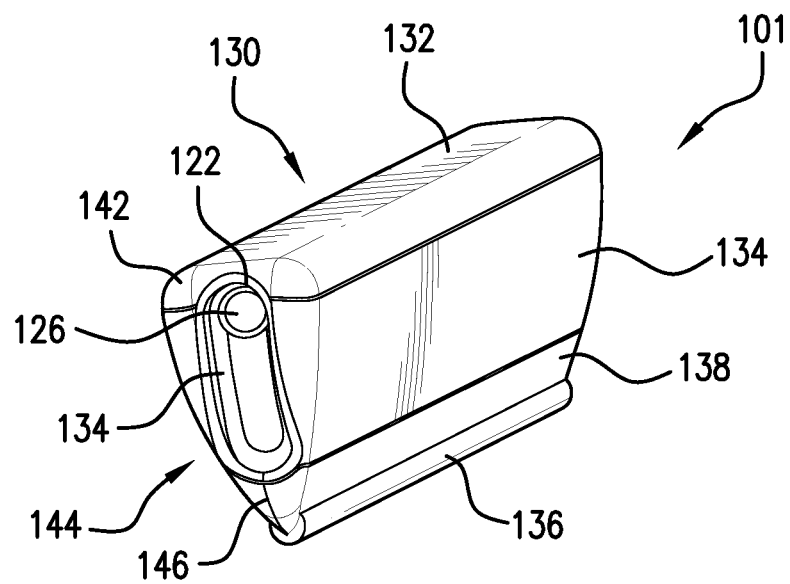
FIG. 5 is a perspective view of the end effector of the electrosurgical device of FIG. 3.
Figure 6:
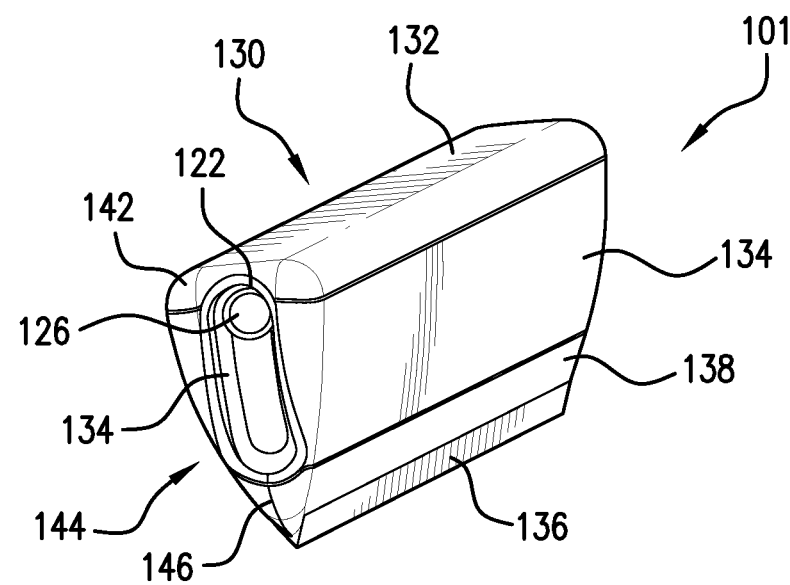
FIG. 6 is a perspective view of an alternative embodiment of the end effector of the electrosurgical device of FIG. 3.

Within handle 100 of device 30, the distal end of fluid delivery tubing 16 may be connected to the proximal end of hollow tube 122 of shaft member 120, as shown in FIGS. 4-6. Shaft member 120 may comprise a self-supporting, electrically conductive tube 122 which may comprise a metal tubing segment, such as stainless steel tubing (e.g. hypodermic tubing). In such case, the outer surface of the tube 122 will preferably be electrically insulated by, for example, an overlying electrical insulator such as provided by polymer shrink wrap. To connect delivery tubing 16 to tube 122, the lumen 18 of delivery tubing is preferably interference fit over the outside diameter of tube 122 to provide an interference fit seal. Fluid 12 then may flow through the lumen 124 of tube 122 and be expelled from fluid outlet opening 126 at the distal end 127 of the tube 122.

Figure 7:
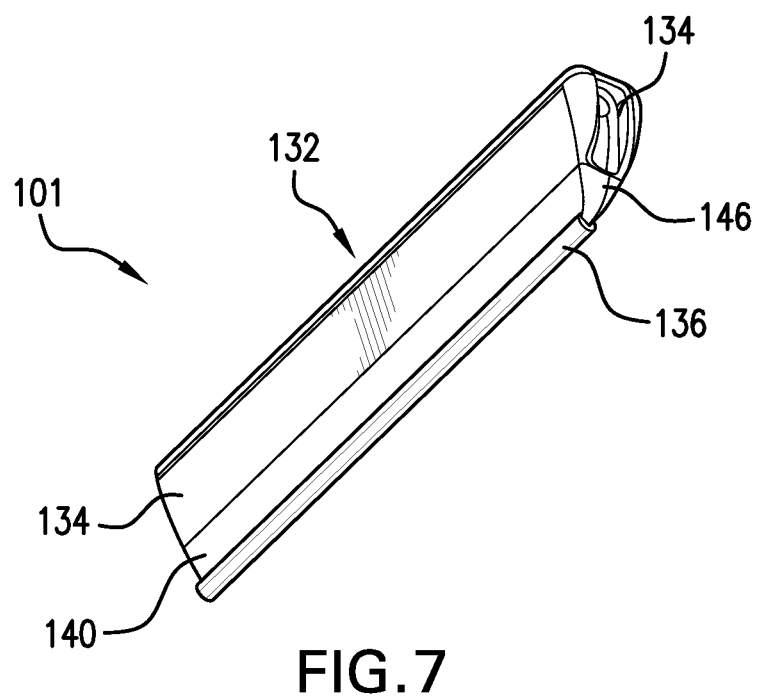
FIG. 7 is another perspective view of the end effector of the electrosurgical device of FIG. 3.

Carried by and connected to a distal end of tube 122 is an end effector 101 in the form of an elongated wedge or triangular shaped blade member 130 having an electrically insulative (i.e., insulating) body portion 132, which may comprise an electrically insulative material such as a polymer or ceramic material. As shown in FIGS. 5 and 7, body portion 132 has opposing planar sides 138, 140 which may be partially covered by overlying electrode 134. Overlying electrode 134 may comprise, for example, a metal or conductive polymer material. In one embodiment, electrode 134 is formed by a thin metallic coating, such as would be provided by a low impedance, conductive paint (e.g., a Pb and Cd Free Silver Conductor C8728, available from Heraeus Materials Technology LLC, Thick Film Material Division, West Conshohocken, Pa.) or by depositing a metal using printed circuit board or semiconductor manufacturing techniques. Also as shown, sides 138, 140 converge to provide a wedge or triangular shape adjacent to electrode 136 which defines an electrosurgical cutting edge of end effector 101.

In one example embodiment, as shown in FIG. 5, electrode 136 may particularly comprise a wire having a rounded, cylindrical shape, with a radius of about 0.5 mm or less and which extends longitudinally (proximally-distally) along a length of body portion 132. In other example embodiments, such as in FIG. 6, edge 136 may be made sharp. This is accomplished, for example, by folding or bending a sheet of metal around the electrosurgical cutting edge formed by converging sides 138, 140 and sanding or grinding the metal to a sharp edge (e.g., having an edge thickness of about 0.005 to 0.010 inches (0.12 mm to 0.25 mm)).

Figure 8:
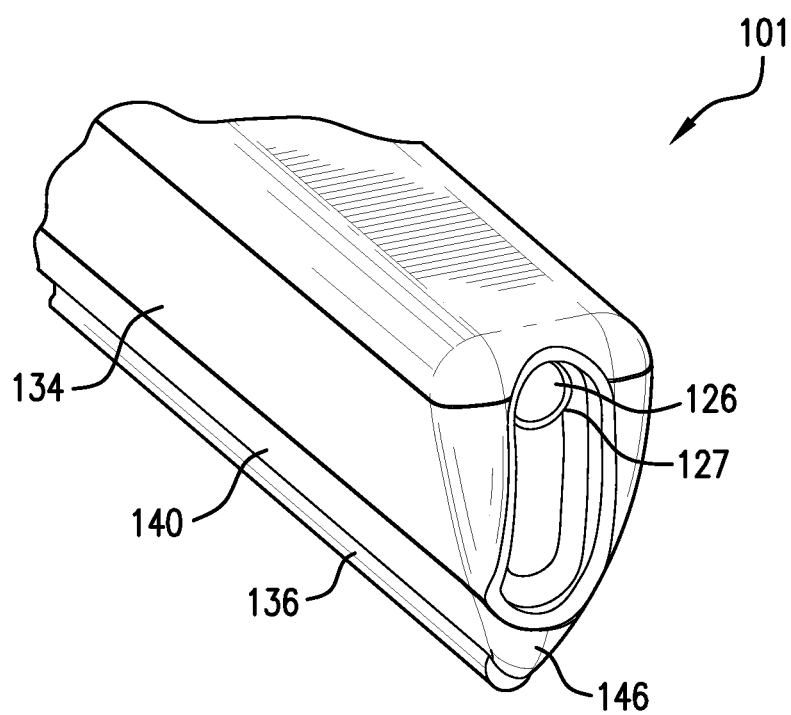
FIG. 8 is a perspective view of a distal end portion of the end effector of the electrosurgical device of FIG. 3.

At the distal end 142 of body portion 132 is an oblong cavity 144 which contains the distal end 127 of tube 122 and fluid outlet opening 126, as shown in FIG. 8. Oblong cavity 144 also has its surface coated with the metallic material to provide electrode 134 since it is in physical contact with electrically conductive tube 122 from which it receives electrical energy. There is also a portion 146 of body portion 132 located between electrodes 134 and 136 at the distal end 142 which functions to minimize or interrupt any short that may occur between electrodes 134 and 136. In addition, portion 146 may reduce or eliminate the ingress of fluid 12 to the vicinity of electrode 136, preventing any impairment of the cutting action by a defocused electric field.

Figure 9:
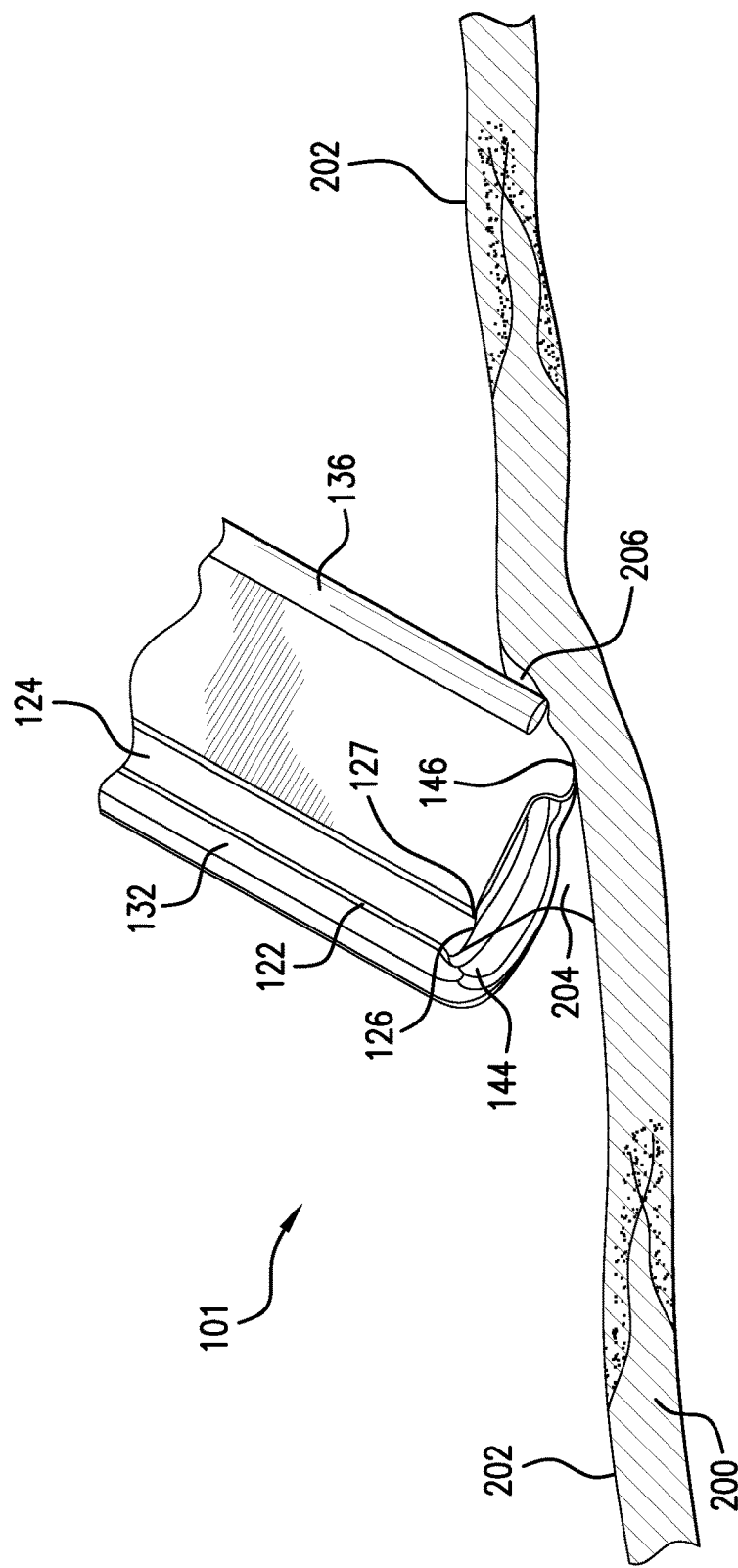
FIG. 9 is a sectional view of a distal end portion of the end effector of the electrosurgical device of FIG. 3 shown in the environment of cutting a biological tissue.

Device 30 is preferably used with an electrically conductive fluid 12. As shown in FIG. 9, in order to facilitate plasma generation, two contacts are made with tissue 200, one contact by cutting electrode 136 and another contact with return electrode The cutting electrode 136 of device 30 may be brought in contact with the tissue 200 to be cut, and power may be applied to the device 30. Depending on the angular position of device 30 with respect to tissue 200, the contact with the return electrode 134 may or may not be established and, as a result, the plasma process may or may not initialize. If there is contact between the return electrode 134 and tissue 200, the plasma process will initialize. If the angle of device 30 is such that there is no contact between return electrode 134 and tissue 200, the plasma process may not initialize.

To overcome this concern and to provide better assurance of electrical contact between return electrode 134 and tissue 200, an electrically conductive fluid 12 dispensed from fluid outlet opening 126 of tube 122, which is conductively coupled to the return electrode 134, may be used to establish a momentary localized fluid coupling 204 which provides an electrically conductive bridge between the return electrode 134 and the tissue 200. Once fluid coupling/bridge 204 is established between the return electrode 134 and the tissue 200, plasma ignition and the cutting process may commence. The fluid coupling/bridge 204 may be replaced by direct contact between the return electrode 134 and the tissue 200 as member 130 advances through the tissue 200. Thus, the fluid coupling/bridge 204 may provide a temporary connection between the return electrode 134 and the tissue 200. Once plasma ignition occurs and cutting is initiated, as shown by plasma area 206, the return electrode 134 may establish a direct connection with the tissue 200, allowing use of the electrically conductive fluid to be terminated. In particular, the flow of fluid 12 from device 30 may be terminated within seconds, for example, about 15 seconds or less, and more particularly about 10 seconds or less. In some cases, fluid flow may be terminated in about 3-5 seconds and, in other cases, in about 0.1-2.0 seconds.

Figure 10:
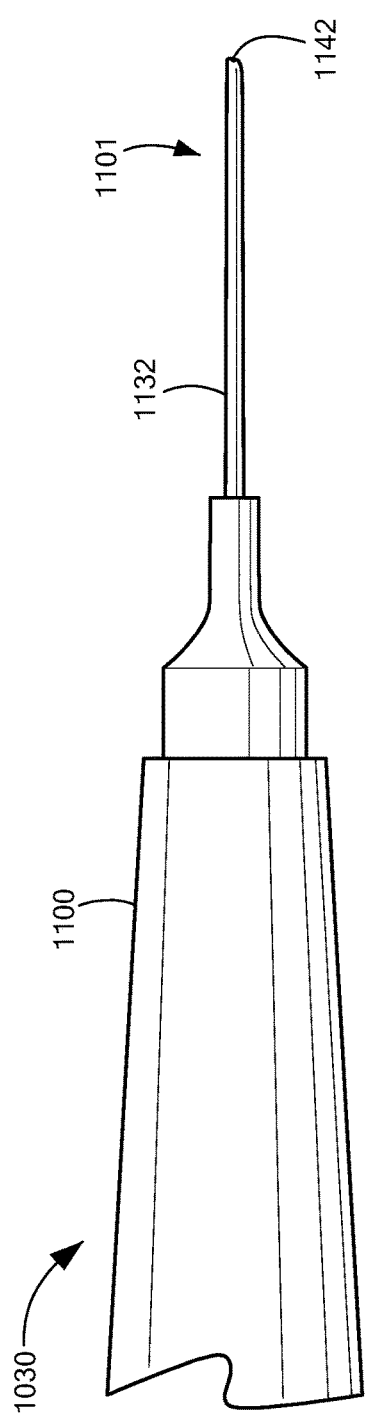
FIG. 10 is a side view of a second embodiment 1030 of the electrosurgical device of the present invention.

FIGS. 11-15 show an alternate embodiment 1030 of electrosurgical device 30. Referring first to FIG. 10, a side view of device 1030 is shown. In this embodiment, device 1030 includes a handle 1100 and an end effector 1101. End effector 1101 includes a body portion 1132 having a distal end 1142.

Figure 11:
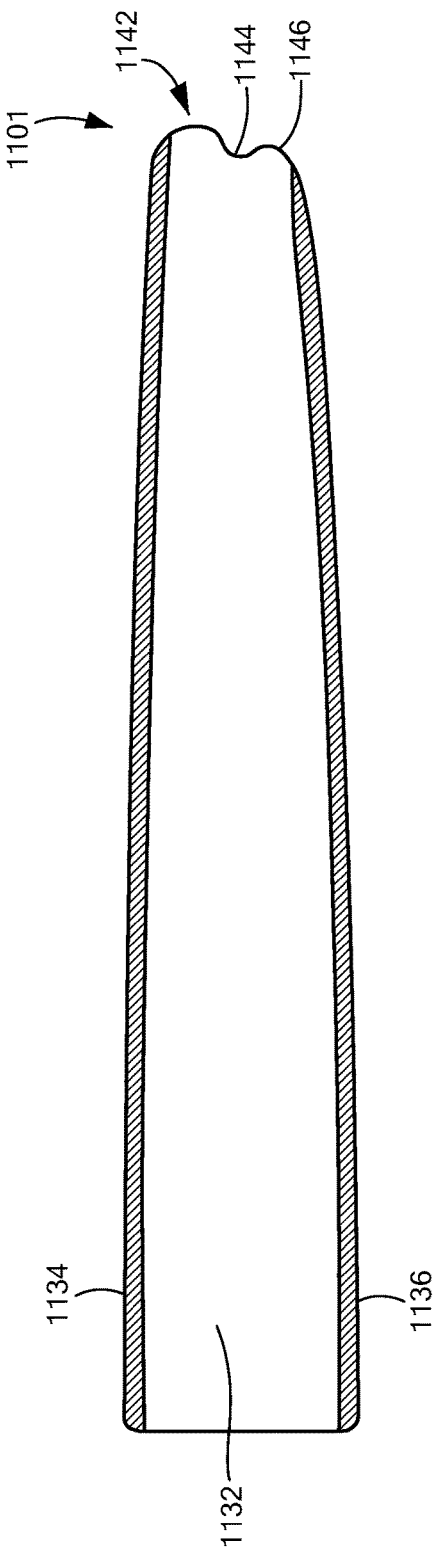
FIG. 11 is a side view of end effector 1101 of electrosurgical device 1030.
Figure 12:
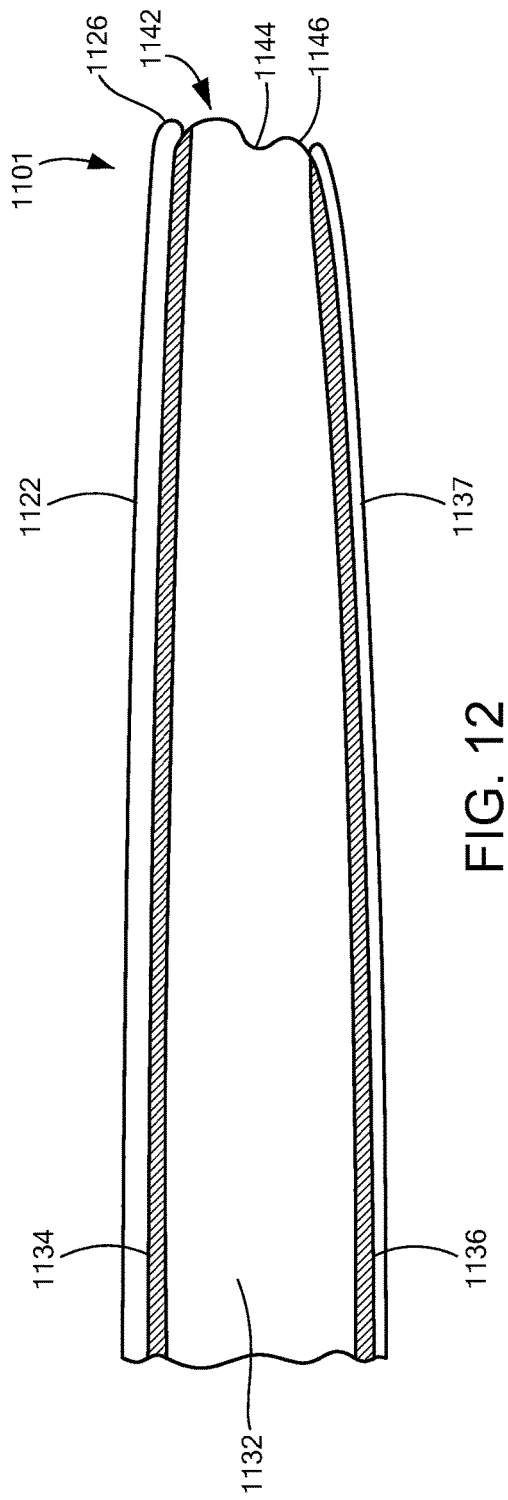
FIG. 12 is a side view of end effector 1101 of electrosurgical device 1030 showing the addition of a conductive tube and a cutting wire.

FIGS. 11 and 12 show a side view of end effector 1101. As shown, end effector 1101 includes a body portion 1132, a cutting electrode 1136 and a return electrode 1134. Distal end 1142 of body portion 1132 includes a cavity or dimple 1144 formed therein. The position of cavity 1144 in distal end 1142 causes formation of a protruding portion 1146 of body portion 1132 to be formed adjacent cavity 1144. Cavity 1144 and protruding portion 1146 act together to prevent direct short-circuits between electrodes 1134 and 1136. In addition, portion 1146 may reduce or eliminate the ingress of conductive fluid to the vicinity of electrode 1136, preventing any impairment of the electrosurgical cutting action by a defocused electric field.

Body portion 1132 is formed from an insulating material such as a ceramic or polymer material. Body portion 1132 has a cross-sectional shape that is substantially rectangular or blade-shaped, having substantially flat, parallel sides. In one example embodiment, body portion 1132 is a thin ceramic blade having a thickness of approximately 0.020 inches (0.51 mm). Electrodes 1134 and 1136 are formed by depositing a thin metal layer, such as would be provided by a low impedance, conductive paint (e.g., Pb and Cd Free Silver Conductor C8728, available from Heraeus Materials Technology LLC, Thick Film Material Division, West Conshohocken, Pa.) or by depositing a metal using printed circuit board or semiconductor manufacturing techniques.

As shown in FIG. 12, an electrically conductive tube 1122 may be attached to electrode 1134 along the length of body portion 1132, where it may also serve as part of (or an alternative for) return electrode 1134. Tube 1122, having a fluid outlet opening 1126 adjacent to distal end 1142, is configured to deliver a conductive fluid to area immediately adjacent to distal end 1142. The embodiment of FIG. 11 also shows a cutting wire 1137 attached to cutting electrode 1136. In an example embodiment, wire 1137 has a diameter of 0.005" to 0.015" (0.13 mm to 0.38 mm) and is soldered (or welded) onto cutting electrode 1136 to enhance durability of cutting electrode 1136.

Figure 13:
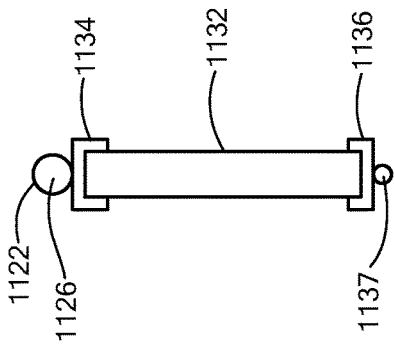
FIG. 13 is a cross-sectional view of end effector 1101 taken near distal end 1142.
Figure 14:
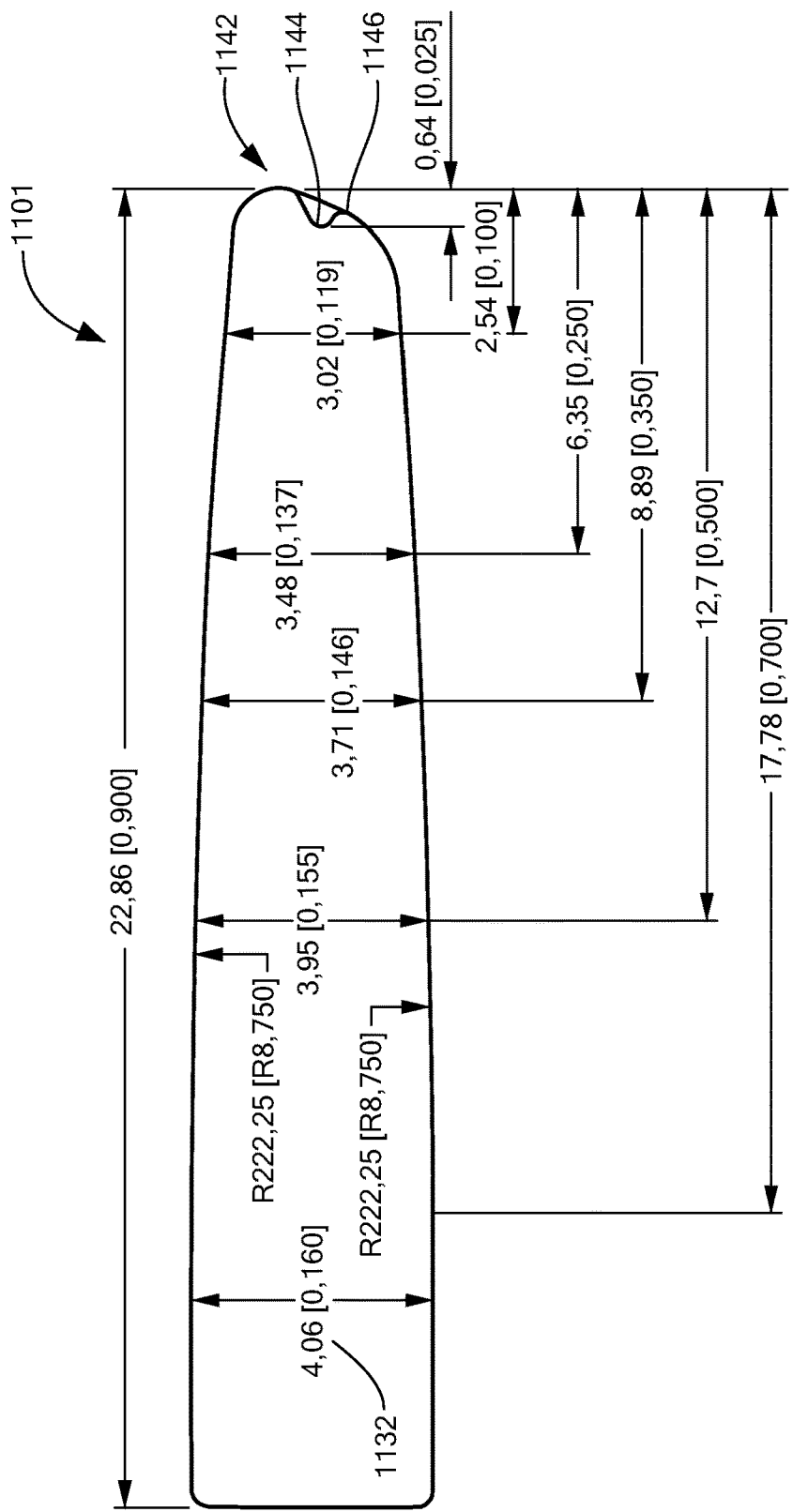
FIG. 14 is a schematic diagram of body portion 1132 of end effector 1101.
Figure 15:
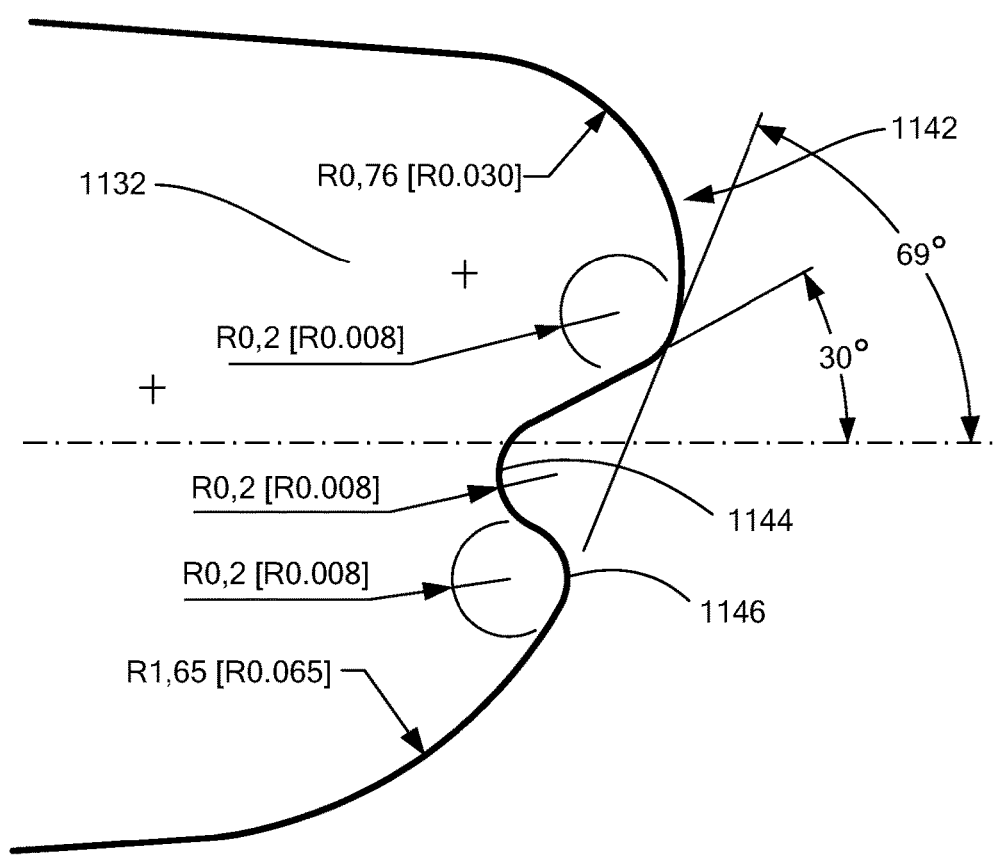
FIG. 15 is a schematic diagram depicting in detail the shape of distal end 1142 of body portion 1132 of end effector 1101.

FIG. 13 shows a cross-sectional view (taken near distal end 1142) of end effector 1101. FIG. 14 is a schematic diagram of body portion 1132 of end effector 1101. FIG. 15 is a schematic diagram depicting in detail the shape of distal end 1142 of body portion 1132 of end effector 1101. These figures serve to further depict the details of this embodiment of the invention.

Figure 16:
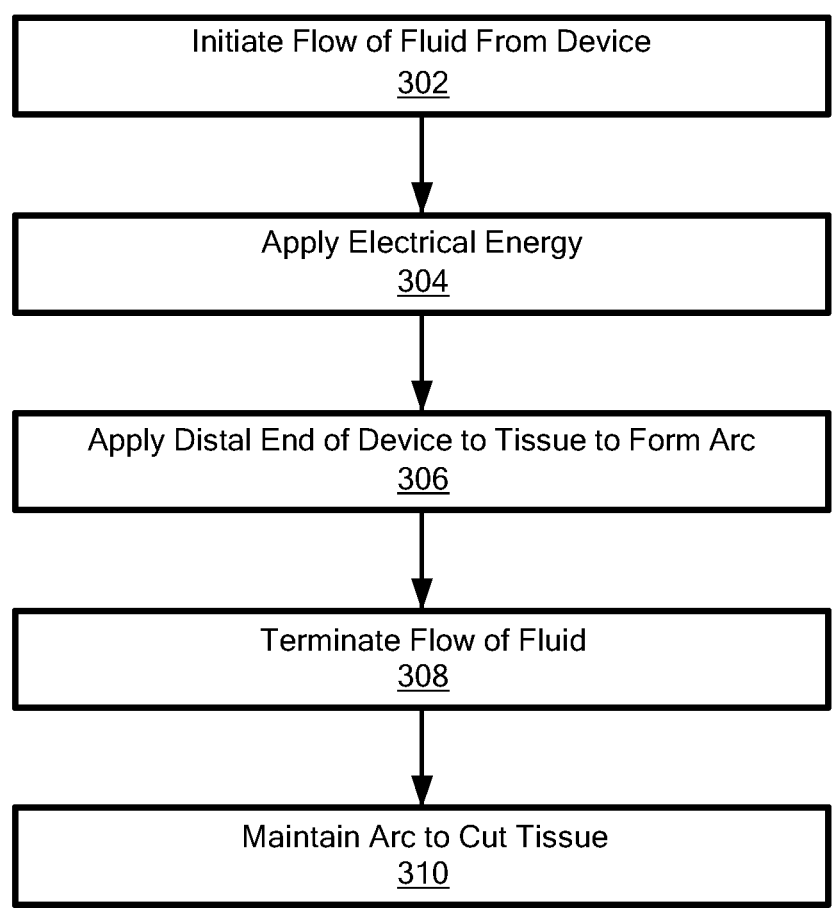
FIG. 16 is a flow chart of an exemplary method for the electrosurgical cutting of biological tissue according to an embodiment of the present invention.

FIG. 16 illustrates a flow chart for the steps performed for cutting biological tissue in accordance with an embodiment of the present invention. At step 302, a flow of an electrically conductive fluid to a distal end of the bipolar electrosurgical device is initiated. At step 304, electrical energy is applied between the first electrode and the second electrode on the bipolar electrosurgical device. At step 306, the bipolar electrosurgical device is applied to the biological tissue such that the first electrode near the distal end of the bipolar electrosurgical device is in direct contact with the biological tissue. This will result in formation of an electrical arc adjacent the distal end of the bipolar electrosurgical device. At step 308, the flow of the electrically conductive fluid may be terminated without affecting the arc. Thus, as shown at step 310, the arc is maintained to cut the biological tissue.

Based on the disclosure set forth herein, a person skilled in the art will understand that the steps of this method are presented in a representative order and that certain of the steps may be performed in a different order or may even be performed simultaneously. For example, steps 302 and 304 may be performed in a different order or may be performed simultaneously.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner in which the invention may be claimed, or that all recited features are necessary.

All publications and patent documents cited in this application are incorporated by reference in their entirety for all purposes to the extent they are consistent.

What is claimed is:

1. A method for electrosurgical cutting of biological tissue, comprising:
 initiating a flow of an electrically conductive fluid to a distal end of a bipolar electrosurgical device, the distal end of the bipolar electrosurgical device including a first electrode adjacent a second electrode;

applying electrical energy between the first electrode and the second electrode on the bipolar electrosurgical device;

positioning the first electrode and the second electrode proximate the biological tissue and forming arc adjacent the distal end of the bipolar electrosurgical device;

terminating the flow of the electrically conductive fluid; and maintaining the arc to cut the biological tissue after terminating the flow of the electrically conductive fluid.

2. The method of claim 1, wherein initiating the flow of the electrically conductive fluid to the distal end of the bipolar electrosurgical device includes delivering the electrically conducting fluid to a cavity in the distal end of the bipolar electrosurgical device.

3. The method of claim 2, wherein the bipolar electrosurgical device includes an insulating body disposed between the first electrode and the second electrode.

4. The method of claim 3, wherein the first electrode protrudes a distance away from the insulating body.

5. The method of claim 4, wherein the cavity is recessed within a portion of the insulating body.

6. The method of claim 5, wherein the bipolar electrosurgical device includes a fluid delivery tube disposed along a surface of the second electrode.

7. The method of claim 1, wherein applying electrical energy includes applying pulsed electrical energy to the biological tissue.

8. The method of claim 1, wherein applying electrical energy includes applying continuous electrical energy to the biological tissue.

9. The method of claim 1, wherein terminating the flow of the electrically conductive fluid includes terminating the flow of the electrically conductive fluid about three to five seconds after initiation of the flow.

10. The method of claim 1, wherein terminating the flow of the electrically conductive fluid includes terminating the flow of the electrically conductive fluid about 0.1 to 2.0 seconds after initiation of the flow.

11. A method for electrosurgical cutting of biological tissue, comprising:

initiating a flow of an electrically conductive fluid to a distal end of a bipolar electrosurgical device, the distal end of the bipolar electrosurgical device including a first electrode adjacent a second electrode;

applying electrical energy between the first electrode and the second electrode on the bipolar electrosurgical device, the first electrode and the second electrode being non-porous;

positioning the first electrode and the second electrode proximate the biological tissue and forming arc adjacent the distal end of the bipolar electrosurgical device;

terminating the flow of the electrically conductive fluid; and maintaining the arc to cut the biological tissue after terminating the flow of the electrically conductive fluid.

12. A method for electrosurgical cutting of biological tissue, comprising:

initiating a flow of an electrically conductive fluid to a distal end of a bipolar electrosurgical device, the distal end of the bipolar electrosurgical device including a first electrode adjacent a second electrode;

applying electrical energy between the first electrode and the second electrode on the bipolar electrosurgical device, the first electrode and the second electrode being substantially coterminous at the distal end of the bipolar electrosurgical device;

positioning the first electrode and the second electrode proximate the biological tissue and forming arc adjacent the distal end of the bipolar electrosurgical device;

terminating the flow of the electrically conductive fluid; and maintaining the arc to cut the biological tissue after terminating the flow of the electrically conductive fluid.

* * * * *